(12) United States Patent
Hestad

(10) Patent No.: US 8,870,924 B2
(45) Date of Patent: Oct. 28, 2014

(54) DYNAMIC VERTEBRAL FASTENER

(75) Inventor: Hugh D. Hestad, Edina, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 1018 days.

(21) Appl. No.: 12/204,691

(22) Filed: Sep. 4, 2008

(65) Prior Publication Data

US 2010/0057126 A1  Mar. 4, 2010

(51) Int. Cl.
*A61B 17/70* (2006.01)
*A61B 17/00* (2006.01)

(52) U.S. Cl.
CPC ........... *A61B 17/7032* (2013.01); *A61B 17/704* (2013.01); *A61B 17/7046* (2013.01); *A61B 17/7005* (2013.01); *A61B 2017/00862* (2013.01)
USPC ........................................................ 606/257

(58) Field of Classification Search
CPC ...................... A61B 17/7037; A61B 17/7038
USPC .......................................... 606/246–279, 331
See application file for complete search history.

(56) References Cited

U.S. PATENT DOCUMENTS

| | | | |
|---|---|---|---|
| 5,910,142 A | 6/1999 | Tatar | |
| 6,802,844 B2 | 10/2004 | Ferree | |
| 6,843,791 B2 * | 1/2005 | Serhan | 606/272 |
| 7,141,051 B2 * | 11/2006 | Janowski et al. | 606/272 |
| 7,261,714 B2 * | 8/2007 | Richelsoph | 606/60 |
| 7,625,394 B2 * | 12/2009 | Molz et al. | 606/270 |
| 7,828,830 B2 * | 11/2010 | Thramann et al. | 606/331 |
| 8,012,177 B2 * | 9/2011 | Jackson | 606/254 |
| 8,043,340 B1 * | 10/2011 | Law | 606/257 |
| 8,092,500 B2 * | 1/2012 | Jackson | 606/254 |
| 8,506,599 B2 * | 8/2013 | Jackson | 606/264 |
| 2004/0143264 A1 | 7/2004 | McAfee | |
| 2004/0225289 A1 * | 11/2004 | Biedermann et al. | 606/61 |
| 2005/0033295 A1 * | 2/2005 | Wisnewski | 606/61 |
| 2005/0143737 A1 | 6/2005 | Pafford et al. | |
| 2005/0182409 A1 * | 8/2005 | Callahan et al. | 606/72 |
| 2005/0216003 A1 * | 9/2005 | Biedermann et al. | 606/61 |
| 2006/0089643 A1 | 4/2006 | Mujwid | |
| 2006/0229615 A1 | 10/2006 | Abdou | |
| 2007/0093821 A1 | 4/2007 | Freudiger | |
| 2007/0118118 A1 | 5/2007 | Kwak et al. | |
| 2007/0161994 A1 | 7/2007 | Lowery et al. | |
| 2007/0233064 A1 * | 10/2007 | Holt | 606/61 |
| 2007/0233087 A1 | 10/2007 | Schlapfer | |
| 2007/0270813 A1 * | 11/2007 | Garamszegi | 606/61 |

(Continued)

FOREIGN PATENT DOCUMENTS

| | | | |
|---|---|---|---|
| WO | 2008013892 A2 | 1/2008 | |
| WO | 2008082085 A1 | 7/2008 | |
| WO | 2008124772 A1 | 10/2008 | |

*Primary Examiner* — Ellen C Hammond
*Assistant Examiner* — Stuart S Bray
(74) *Attorney, Agent, or Firm* — Seager, Tufte & Wickhem, LLC

(57) ABSTRACT

A spinal fixation assembly for connecting an elongate member along a region of a spinal column with a plurality of fasteners is disclosed. The spinal fixation assembly comprises a threaded fastener having a first threaded end region and a second end region configured to receive an elongate member, such as a rod. A locking member is included for securing the elongate member within the second end region. The second end region and the locking member include elastomeric members that contact the elongate member to allow for a degree of dynamic movement.

32 Claims, 17 Drawing Sheets

(56) References Cited

U.S. PATENT DOCUMENTS

| | | |
|---|---|---|
| 2008/0021465 A1 | 1/2008 | Shadduck et al. |
| 2008/0177321 A1* | 7/2008 | Drewry et al. ............... 606/266 |
| 2009/0005817 A1* | 1/2009 | Friedrich et al. ............ 606/246 |
| 2009/0105762 A1* | 4/2009 | Jackson ....................... 606/246 |
| 2009/0240285 A1* | 9/2009 | Friedrich et al. ............ 606/255 |
| 2009/0281574 A1* | 11/2009 | Jackson ....................... 606/264 |
| 2009/0326584 A1* | 12/2009 | Slivka et al. ................ 606/261 |
| 2010/0010543 A1* | 1/2010 | Jackson ....................... 606/254 |
| 2010/0179602 A1* | 7/2010 | Dauster et al. .............. 606/308 |
| 2010/0191289 A1* | 7/2010 | Ludwig et al. .............. 606/264 |
| 2010/0234891 A1* | 9/2010 | Freeman et al. ............. 606/266 |
| 2010/0274290 A1* | 10/2010 | Jung et al. ................... 606/264 |
| 2011/0295320 A1* | 12/2011 | Jackson ....................... 606/264 |
| 2012/0130432 A1* | 5/2012 | Ferree et al. ................ 606/279 |
| 2012/0221054 A1* | 8/2012 | Jackson ....................... 606/254 |
| 2012/0239090 A1* | 9/2012 | Abdou ......................... 606/264 |
| 2012/0310287 A1* | 12/2012 | Bao et al. .................... 606/279 |

* cited by examiner

DYNAMIC VERTEBRAL FASTENER

TECHNICAL FIELD

The disclosure is directed to a system, apparatus and method for providing stabilization to one or more vertebrae of a spinal column. More particularly, the disclosure is directed to a system, apparatus and method for providing dynamic stability or support to one or more spinal segments of a spinal column.

BACKGROUND

The spinal column of a patient includes a plurality of vertebrae linked to one another by facet joints and an intervertebral disc located between adjacent vertebrae. The facet joints and intervertebral disc allow one vertebra to move relative to an adjacent vertebra, providing the spinal column a range of motion. Diseased, degenerated, damaged, or otherwise impaired facet joints and/or intervertebral discs may cause the patient to experience pain or discomfort and/or loss of motion, thus prompting surgery to alleviate the pain and/or restore motion of the spinal column.

Accordingly, there is an ongoing need to provide alternative apparatus, devices, assemblies, systems and/or methods that can function to alleviate pain or discomfort, provide stability, such as dynamic stability, and/or restore a range of motion to a spinal segment of a spinal column.

SUMMARY

The disclosure is directed to several alternative designs, materials and methods of manufacturing spinal fixation hardware, structures, and assemblies.

Some embodiments of the invention are directed to a spinal fixation assembly for connecting an elongate member along a region of a spinal column with a plurality of fasteners. In some embodiments, the spinal fixation assembly may comprise an elongate member and a threaded fastener having a first threaded end region and a second end region configured to receive the elongate member, such as a rod. A locking member may be used for securing the elongate member within a channel of the second end region. The second end region and/or the locking member may include elastomeric members that may contact the elongate member when the elongate member is secured in the channel of the second end region. The elastomeric members may flex under pressure to allow some dynamic movement between the elongate member and the second end region of the threaded fastener when installed. In some embodiments, the elongate member may further comprise spherical collars. The collars may fit into recesses in the elastomeric members in order to prevent slippage of the elongate member within the second end region.

Some embodiments of the invention are directed to a spinal fixation assembly for connecting an elongate member along a region of a spinal column with a plurality of fasteners. The spinal fixation assembly may include a vertebral anchor, such as a pedicle screw, or other threaded fastener, having a first threaded end for engaging the vertebrae and second U-shape end region defining a channel. An elongate member may extend through the channel of the U-shape end region. The elongate member may be secured within the channel using a locking member. The locking member and the channel of the second end region of the threaded fastener may each include an elastomeric member. The elongate member may be positioned between the elastomeric members such that the elongate member contacts the elastomeric members. The contact between the elastomeric members and the elongate member may allow for dynamic angular displacement of the elongate member relative to the second end region of the threaded fastener.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
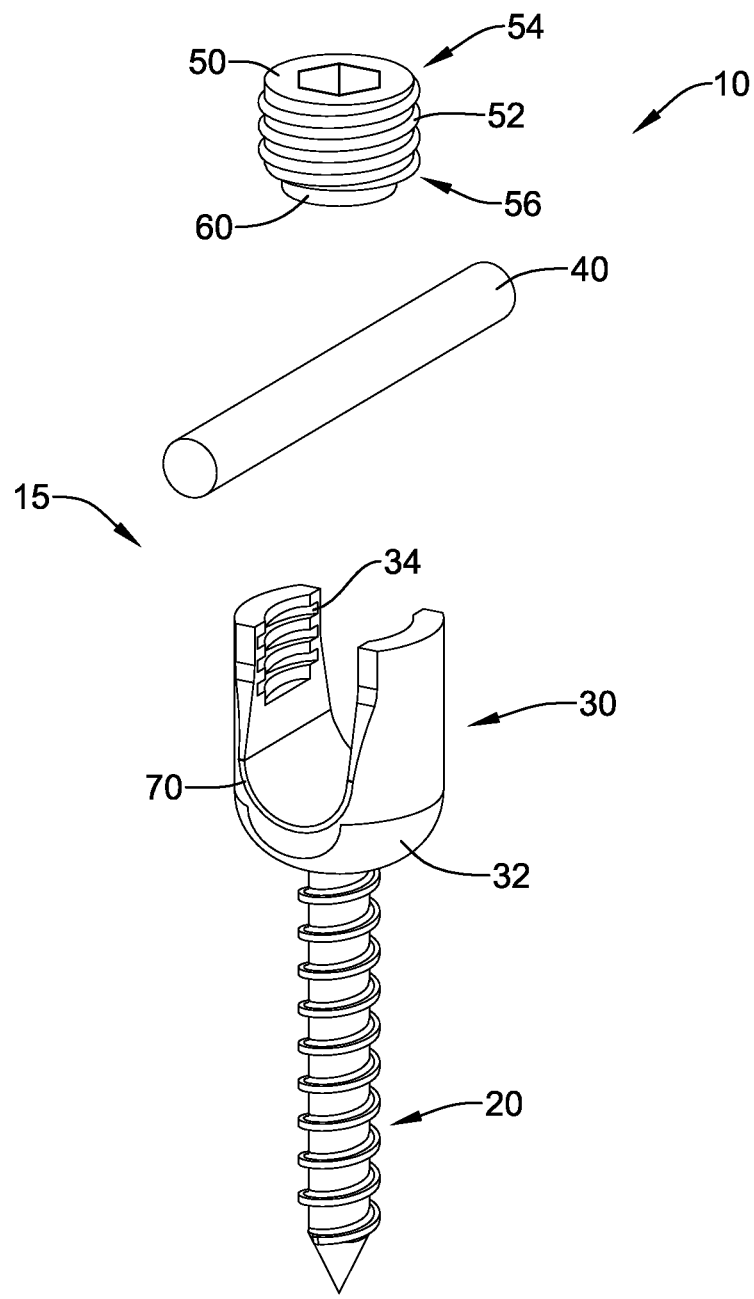
FIG. 1 is an exploded view of an illustrative spinal fixation assembly.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Now referring to the drawings, FIG. 1 is an exploded view of an illustrative spinal fixation assembly 10 for connecting an elongate member along a region of a spinal column with a plurality of fasteners. The assembly 10 may allow for a degree of dynamic movement (e.g. angular movement) between the elongate member and the fasteners. The spinal fixation assembly 10 may include a fastener 15, such as a threaded fastener, having a first region 20, which in some embodiments may be a threaded end region, for engaging the spinal column and a second region 30, which may in some embodiments be an end region of the fastener 15 for receiving the elongate member. While the spinal fixation assembly 10 is shown as including threaded fasteners 15, other devices, such as vertebral hooks (e.g. laminar hooks), may be used to secure the assembly 10 to the spinal column. It is contemplated that the spinal fixation assembly 10 may comprise a pedicle screw assembly. While the current embodiment illustrates the second region 30 as fixedly attached to the first region 20, the first region 20 and the second region 30 may be designed for movement relative to one another for positioning and may be lockable in a desired position (e.g. polyaxial screws). Some exemplary polyaxial screws which may be suitable for the assembly 10 are disclosed in U.S. Pat. No. 7,335,201 and U.S. Pat. App. Pub. Nos. 2006/0089643 and 2006/0052786, each of which is incorporated herein by reference.

In some embodiments, the second region 30 of the fastener 15 may have a channel in a saddle 32, which in some cases may be U-shaped, to receive an elongate member 40 or other connecting portion configured to be connected to an elongate member 40. The second region 30 may be of any shape desired capable of receiving the elongate member 40. For example, second region 30 may comprise an annular ring for receiving the elongate member 40 through an inner diameter. As shown in FIG. 1, the second region 30 may further include a threaded region 34 such as an internally threaded region. In other embodiments, the threaded region 34 may be an externally threaded region. The saddle 32 of the second end region 30 may further include an elastomeric member 70, which in some embodiments may be an elastomeric insert. In some embodiments the elastomeric member 70 may be disposed on and/or in contact with a surface of the channel of the saddle 32.

In some embodiments, the elastomeric member 70 may be removably attached to the second region 30 and in other embodiments the elastomeric member 70 may be permanently attached to the second region 30. In some embodiments, the elastomeric member 70 may be secured to the second region 30 with any desired means, for example, an adhesive, insert molded, press fit, interlocking, threaded connection, or any other method that will suitably secure the elastomeric member 70 to a surface of the second region 30. In other embodiments, the elastomeric member 70 may not be physically secured to the second region 30, but instead may be held between the elongate member 40 and the second region 30 by the force of the elongate member 40 and a locking member 50.

The elastomeric member 70, which may be placed in contact with the elongate member 40, may flex under pressure to allow some dynamic movement between the elongate member 40 and the second region 30 of the fastener 15. This may cause the elastomeric member 70 to compress or deform to create an articulating surface between the elongate member 40 and the second region 30 of the fastener 15. The elastomeric member 70 may comprise a compressible, polymeric, or otherwise deformable material such as ultra high molecular weight polyethylene (UHMWPE), polyurethane (e.g., polycarbonate-urethane (PCU)), silicone, elastomers, non-elastomers, or any other suitable polymer or plastic. The elastomeric member 70 may have a degree of flexibility to allow the elongate member 40 to deform the elastomeric member 70. This may allow for a certain degree of movement of the elongate member 40 relative to the second region 30 of the fastener 15.

Additionally, spinal fixation assembly 10 may include an elongate member 40, such as an elongate rod, bar, plate, or the like. While the elongate member 40 is shown as having a circular cross section, the elongate member 40 may have a cross section of any desired shape, including, but not limited to: square, rectangular, polygonal, or elliptical. The elongate member 40 may be configured to be connected between a plurality of fasteners 15 to extend between two, three, four, or more vertebrae of the spinal column. The elongate member 40 may be of any length necessary to extend between two, three, four, or more vertebrae of the spinal column. For example, the elongate member 40 may be greater than 0.5 inches, 0.8 inches, 1.0 inch, 2.0 inches or more in length or other length as desired.

The spinal fixation assembly 10 may also include a locking member 50 configured to secure the elongate member 40 within the channel of the U-shape saddle 32 of the second region 30 of the fastener 15. In some embodiments, the locking member 50 may include a first end region 54 and a second end region 56 with a threaded region 52 disposed therebetween. In some embodiments, the threaded region 52 may be an externally threaded region complementary to an internally threaded region 34 of second region 30. In other embodiments, the threaded region 52 may be an internally threaded region complementary to an externally threaded region 134 (shown in FIG. 11) of the second region 30 of the fastener 15. The locking member 50 may further include an elastomeric member 60, which in some embodiments may be an elastomeric insert. In some embodiments the elastomeric member 60 may be disposed on and/or in contact with a surface of the locking member 50.

In some embodiments, the elastomeric member 60 may be removably attached to the locking member 50 and in other embodiments the elastomeric member 60 may be permanently attached to the locking member 50. In some embodiments, the elastomeric member 60 may be secured to the locking member 50 with any desired means, for example, an adhesive, insert molded, press fit, interlocking, threaded connection, or any other method that will suitably secure the elastomeric member 60 to the locking member 50. In other embodiments, the elastomeric member 60 may not be physically secured to the locking member 50, but may be may be held between the elongate member 40 and the locking member 50 by the force of the locking member 50.

The elastomeric member 60 may flex under pressure to allow some dynamic movement between the elongate member 40 and the second region 30 of the threaded fastener 15. This may cause the elastomeric member 60 to compress or deform to create an articulating surface between the elongate member 40 and the second region 30 of the threaded fastener 15. The elastomeric member 60 may comprise a compressible or otherwise deformable material such as ultra high molecular weight polyethylene (UHMWPE), polyurethane (e.g., polycarbonate-urethane (PCU)), silicone, elastomers, non-elastomers, or any other suitable polymer or plastic. The elastomeric member 60 may have a degree of flexibility to allow the elongate member 40 to deform the elastomeric member 60. This may allow for a certain degree of movement of the elongate member 40 relative to the second region 30 of the fastener 15. In some embodiments, elastomeric member 60 may have a diameter smaller than or substantially equal to the diameter of the locking member 50. While the embodiments discussed herein are described with both the second region 30 and the locking member 50 each having an elastomeric member 70,60, it is contemplated that some embodiment may only have one elastomeric insert disposed either within the second region 30 or on the locking member 50.

Figure 2:
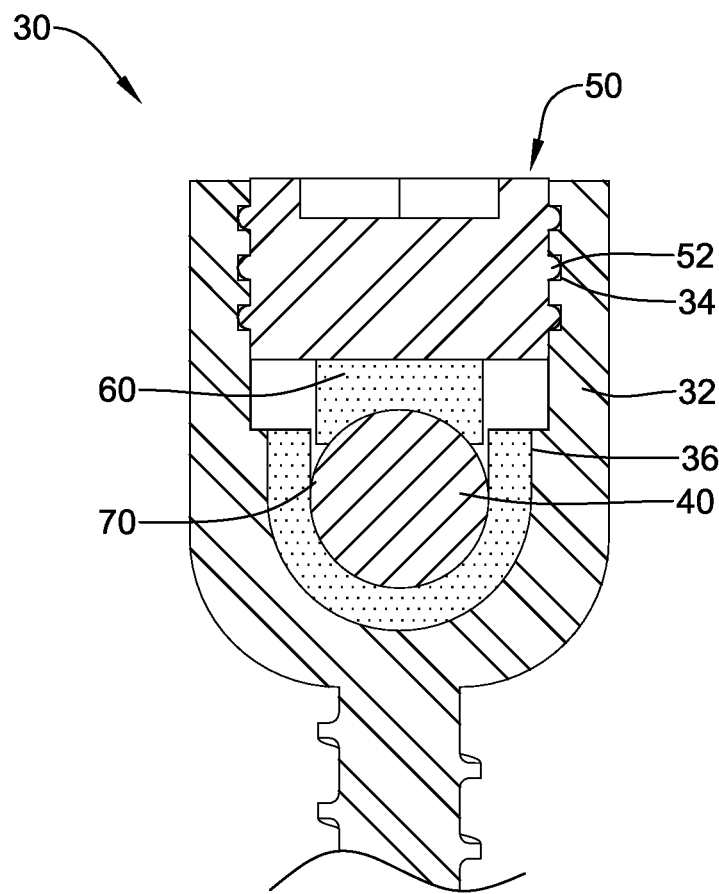
FIG. 2 is an axial cross-section of the assembled illustrative spinal fixation assembly of FIG. 1.

FIG. 2 shows an assembled cross section of the illustrative spinal fixation assembly 10 of FIG. 1. When locking member 50 is threadably engaged with the threaded region 34 of the second region 30 of the fastener 15, elastomeric member 60 and elastomeric member 70 may contact the elongate member 40. The elastomeric members 60 and 70 may deform under pressure around the elongate member 40 conforming, at least in part, to an outer surface of the elongate member 40. The flexibility of the elastomeric members 60, 70 may allow for a degree of dynamic movement between the elongate member 40 and the fastener 15 when installed. In some embodiments, the elastomeric member 70 may define a portion of the channel and/or may extend up the internal wall 36 of saddle 32 or toward the locking member 50. It is contemplated that in some embodiments the elastomeric member 70 may extend only partially up the internal wall 36 towards the locking member 50. In some embodiments, the elastomeric member 70 may extend the entire depth of the second region 30 from a first side surface to a second side surface or across only a portion of the depth of second region 30. While the elastomeric member 70 is shown having a U-shape in FIG. 2, in other embodiments the elastomeric member 70 may be of any other shape desired to adequately receive and/or contact the elongate member 40. The presence of the elastomeric member 70 may prevent the elongate member 40 from directly contacting the saddle 32 of the fastener 15.

Figure 3:
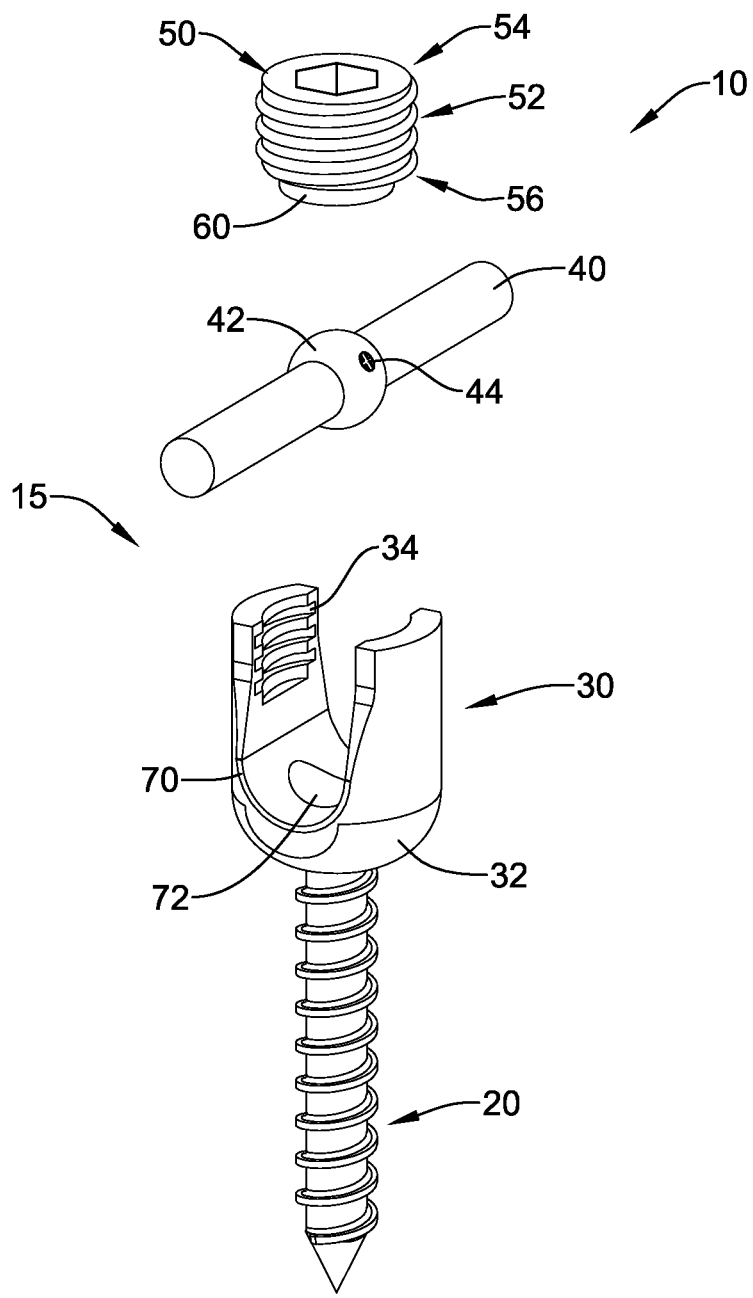
FIG. 3 is an exploded view of another illustrative spinal fixation assembly.

In some embodiments, the elongate member 40 may include a spherical collar 42, as shown in FIG. 3. In some embodiments, the spherical collar 42 may be removable and/or slidable along the elongate member 40, and may be secured to the elongate member 40 by any desired means, such as a tightening screw 44. In some embodiments, the collar 42 may be a separate member that is permanently affixed to the elongate member 40 using suitable affixation techniques, e.g., welding, brazing, soldering, adhesives, etc. In other embodiments the collar 42 may be a unitary portion of the elongate member 40. The elongate member 40 may include one, two, three, or more spherical collars 42 disposed along the elongate member 40 to accommodate any desired number of fasteners 15 being connected therewith.

Figure 4:
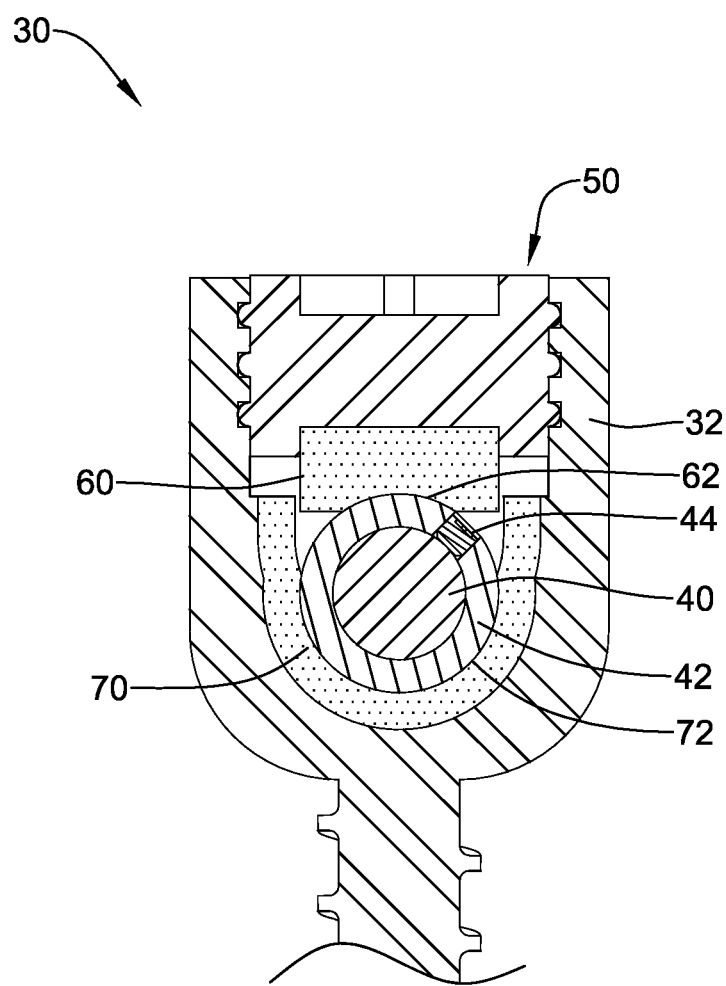
FIG. 4 is an axial cross-section of the assembled illustrative spinal fixation assembly of FIG. 3.

In some embodiments, the elastomeric member 70 may include a concave recess 72 to receive a portion of the spherical collar 42. Additionally or alternatively, the elastomeric member 60 may also include a concave recess 62, as best shown in FIG. 4, to receive a portion of spherical collar 42. In some embodiments, the concave surfaces 62,72 may conform to and contact the convex surface of the spherical collar 42. In some embodiments, the recesses 62,72 may allow more surface area of the elongate member 40 to contact the elastomeric members 60,70, which may capture or prevent at least some longitudinal or axial movement of the elongate member 40. The recesses 62,72 may surround the collar 42 and may help prevent slippage of the elongate member 40 when it is secured within the saddle 32 of the second end region 30 of the threaded fastener 15. While the collar 42 is shown as a sphere, in other embodiments, the collar 42 may be of any geometric shape, including, but not limited to: cubes, rectangular prisms, polygons, or cylinders. Thus, it is contemplated that the recesses 62,72 in the elastomeric members 60,70 may be of any shape desired to receive the collar 42.

FIG. 4 shows an assembled cross section of the illustrative spinal fixation assembly 10 of FIG. 3. As shown in FIG. 4, the spherical collar 42 may contact the elastomeric member 70 at the spherical recess 72 and/or the elastomeric member 60 at the spherical recess 62. In some embodiments, the spherical recesses 62 and 72 may surround at least a portion of the spherical collar 42 to allow for a degree of dynamic movement between the elongate member 40 and the fastener 15. The recesses 62,72 may allow more surface area of the elongate member 40 to contact the elastomeric members 60,70, which may allow for a more uniform clamping force to be applied to the elongate member 40. The spherical collar 42 in combination with the concave recesses 62 and 72 may resist slippage of the elongate member 40 when the locking member 50 is threadably engaged with the second end region 30 of the fastener 15. As the locking member 50 is further engaged with the threaded region 34 of the second region 30, the elastomeric members 60 and 70 may further surround around the spherical collar 42.

Figure 5:
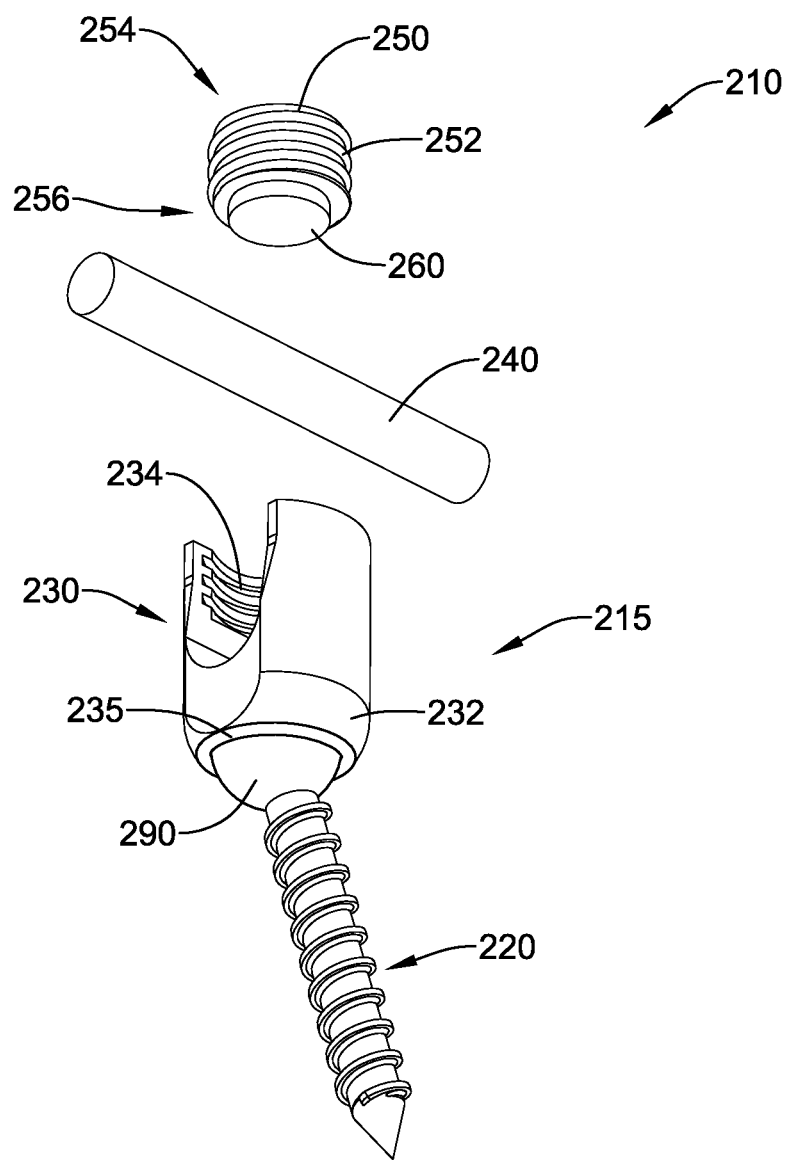
FIG. 5 is an exploded view of another illustrative spinal fixation assembly.

In some embodiments, the spinal fixation assembly 10 may comprise a polyaxial screw. Some exemplary polyaxial screws which may be suitable for the assembly 10 are disclosed in U.S. Pat. No. 7,335,201 and U.S. Pat. App. Pub. Nos. 2006/0089643 and 2006/0052786, each of which is incorporated herein by reference. An exploded view of an illustrative spinal fixation assembly 210, including a polyaxial screw 215, is shown in FIG. 5. The spinal fixation assembly 210 may include a polyaxial screw 215, having a first region 220, which in some embodiments may be a threaded end region, for engaging the spinal column and a second region 230, which may in some embodiments be an end region of the fastener 215 for receiving the elongate member 240. The first region 220 and the second region 230 may be designed for movement relative to one another for positioning and may be lockable in a desired position. In some embodiments, the second region 230 of the fastener 15 may have a channel in a saddle 232, which in some cases may be U-shaped, to receive an elongate member 240 or other connecting portion configured to be connected to an elongate member 240. The second region 230 may be of any shape desired capable of receiving the elongate member 240. First end region 220 may include a spherical or semi-spherical connector 290. Second end region 230 may comprise an opening 235 such that first end region 220 may be disposed in the opening 235. The opening 235 may be smaller than the connector 290 such that the connector 290 may be at least partially located within the saddle 232.

Figure 6:
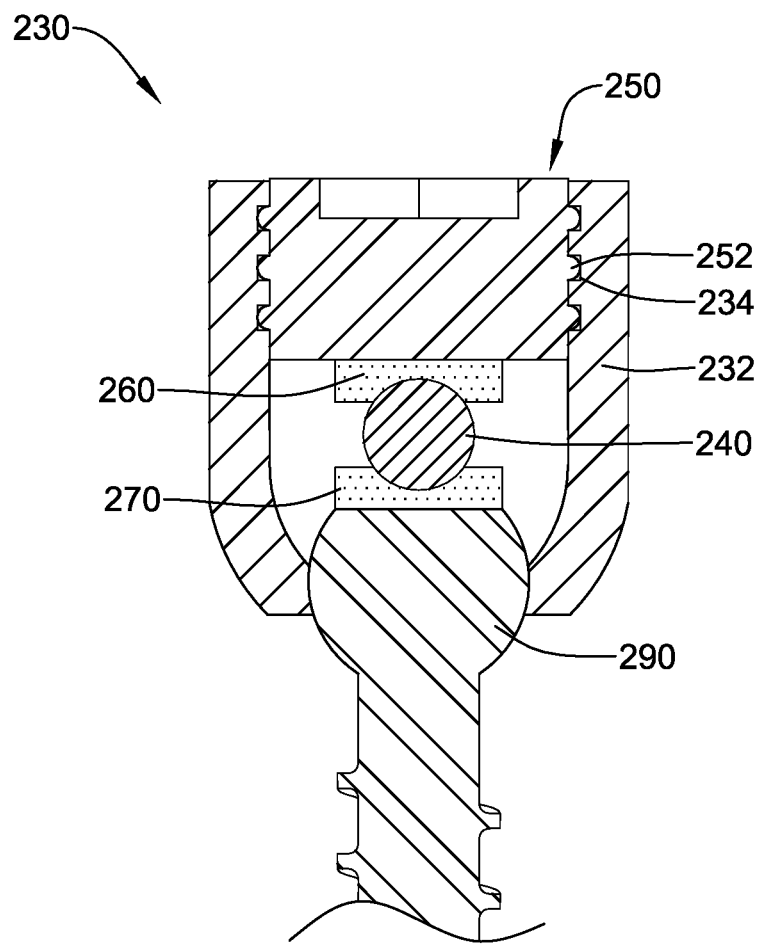
FIG. 6 is an axial cross-section of the assembled illustrative spinal fixation assembly of FIG. 3.

In some embodiments, the connector 290 may further include an elastomeric member 270 (See FIG. 6). In some embodiments, the elastomeric member 270 may be removably attached to the connector 290 and in other embodiments the elastomeric member 270 may be permanently attached to the connector 290. In some embodiments, the elastomeric member 270 may be secured to the connector 290 with any desired means, for example, an adhesive, insert molded, press fit, interlocking, threaded connection, or any other method that will suitably secure the elastomeric member 270 to the connector 290. In other embodiments, the elastomeric member 270 may not be physically secured to the connector 290, but instead may be held between the elongate member 240 and the connector 290 by the force of the elongate member 240 and a locking member 250. It is contemplated that in some embodiments, the connector 290 may not include an elastomeric member 270.

The elastomeric member 270, which may be placed in contact with the elongate member 240, may flex under pressure to allow some dynamic movement between the elongate member 240 and the connector 290 of the fastener 215. This may cause the elastomeric member 270 to compress or deform to create an articulating surface between the elongate member 240 and the connector 290 of the fastener 215. The elastomeric member 270 may comprise a compressible, polymeric, or otherwise deformable material such as ultra high molecular weight polyethylene (UHMWPE), polyurethane, silicone, polycarbonate-urethane (PCU), elastomers, non-elastomers, or any other suitable polymer or plastic. The elastomeric member 270 may have a degree of flexibility to allow the elongate member 240 to deform the elastomeric member 270. This may allow for a certain degree of movement of the elongate member 240 relative to the second region 230 of the fastener 215.

Additionally, spinal fixation assembly 210 may include an elongate member 240, such as an elongate rod, bar, plate, or the like. While the elongate member 40 is shown as having a circular cross section, the elongate member 240 may have a cross section of any desired shape, including, but not limited to: square, rectangular, polygonal, or elliptical. The elongate member 40 may be configured to be connected between a plurality of fasteners 215 to extend between two, three, four, or more vertebrae of the spinal column. The elongate member 240 may be of any length necessary to extend between two, three, four, or more vertebrae of the spinal column. For example, the elongate member 40 may be greater than 0.5 inches, 0.8 inches, 1.0 inch, 2.0 inches or more in length or other length as desired.

The spinal fixation assembly 210 may also include a locking member 250 configured to secure the elongate member 240 within the channel of the U-shape saddle 232 of the second region 230 of the fastener 215. In some embodiments, the locking member 250 may include a first end region 254 and a second end region 256 with a threaded region 252 disposed therebetween. In some embodiments, the threaded region 252 may be an externally threaded region complementary to an internally threaded region 234 of second region 230. The locking member 250 may further include an elastomeric member 260, which in some embodiments may be an elastomeric insert.

In some embodiments, the elastomeric member 260 may be removably attached to the locking member 250 and in other embodiments the elastomeric member 260 may be permanently attached to the locking member 250. In some embodiments, the elastomeric member 260 may be secured to the locking member 250 with any desired means, for example, an adhesive, insert molded, press fit, interlocking, threaded connection, or any other method that will suitably secure the elastomeric member 260 to the locking member 250. In other embodiments, the elastomeric member 260 may not be physically secured to the locking member 250, but may be may be held between the elongate member 240 and the locking member 250 by the force of the locking member 50.

The elastomeric member 260 may flex under pressure to allow some dynamic movement between the elongate member 240 and the second region 230 of the threaded fastener 215. This may cause the elastomeric member 260 to compress or deform to create an articulating surface between the elongate member 240 and the second region 230 of the threaded fastener 215. The elastomeric member 260 may comprise a compressible or otherwise deformable material such as ultra high molecular weight polyethylene (UHMWPE), polyurethane, silicone, polycarbonate-urethane (PCU), elastomers, non-elastomers, or any other suitable polymer or plastic. The elastomeric member 260 may have a degree of flexibility to allow the elongate member 40 to deform the elastomeric member 260. This may allow for a certain degree of movement of the elongate member 240 relative to the second region 230 of the fastener 215. In some embodiments, elastomeric member 260 may have a diameter smaller than or substantially equal to the diameter of the locking member 250.

FIG. 6 shows an assembled cross section of the illustrative spinal fixation assembly 210 of FIG. 5. As shown in FIG. 6, the connector 290 may be disposed within the saddle 232 of the second end region 230. When locking member 250 is threadably engaged with the threaded region 234 of the second region 230 of the fastener 215, elastomeric member 260 and elastomeric member 270 may contact the elongate member 240. The elastomeric members 260 and 270 may deform under pressure around the elongate member 240 conforming, at least in part, to an outer surface of the elongate member 240. The flexibility of the elastomeric members 260, 270 may allow for a degree of dynamic movement between the elongate member 240 and the fastener 215 when installed. It is contemplated that in some embodiments the elastomeric member 270 may have a surface area smaller than or substantially equal to the surface area of the connector 290. The presence of the elastomeric member 270 may prevent the elongate member 240 from directly contacting the connector 290 or saddle 232 of the fastener 215.

Figure 7:
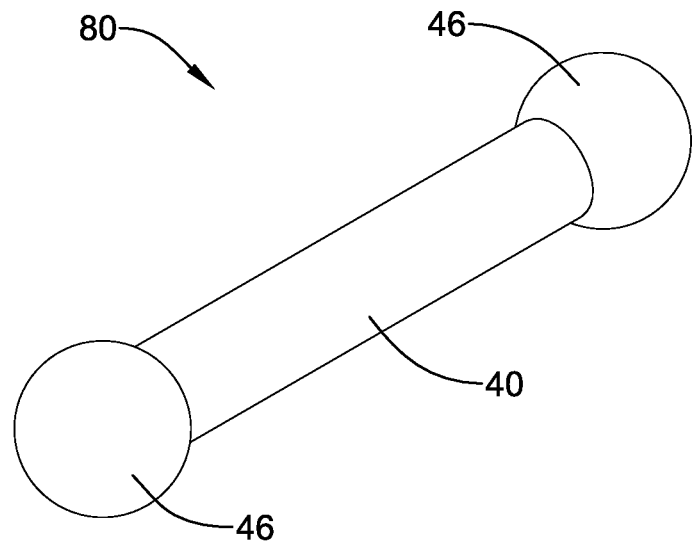
FIG. 7 is an alternate embodiment of the elongate member shown in FIG. 3.

In some embodiments, the spherical member 46 and elongate member 40 may form a unitary elongate member 80 as shown in FIG. 7. The elongate member 40 may have a first spherical member 46 at one end and a second spherical member 46 at the other end. In some embodiments, the elongate member 80 may include one or more additional spherical member 46 located at a position intermediate the first end and the second end of the elongate member 80. The unitary elongate member 80 may be available in a range of lengths to accommodate different spacing between adjacent vertebrae. For example, the length may be about 0.5 inches, 0.8 inches, or 1.0 inch or more in length, or any other desired length. While the member 46 is shown as a sphere, in other embodiments, the member 46 may be of any shape, such as a geometric shape, including, but not limited to: cubes, rectangular prisms, polygons, or cylinders.

Figure 8:
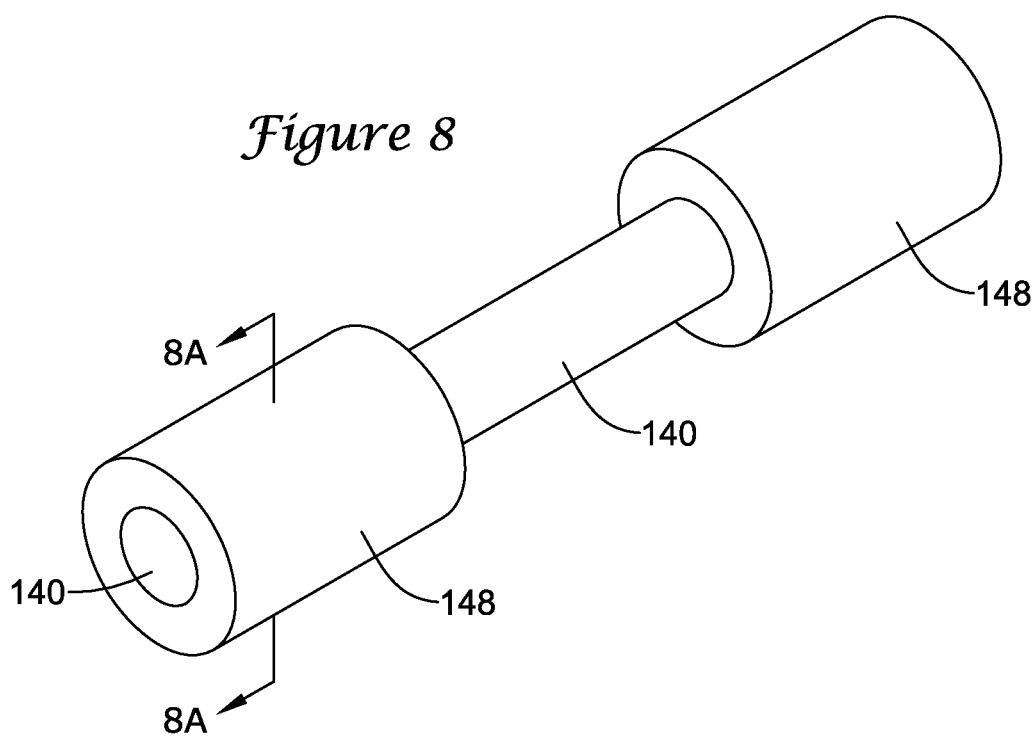
FIG. 8 is an alternate embodiment of the elongate member shown in FIG. 3.

FIG. 8 shows another embodiment of the elongate member 140. In some embodiments, the elastomeric member 148 may surround the elongate member 140. The elastomeric member 148 may encase the elongate member 140. The elastomeric member 148 may cover only a portion of the elastomeric member 140 as shown in FIG. 8. In other embodiments, the elastomeric member 148 may fully surround the elongate member 140 for the entire length of the elongate member 140. In some embodiments, the elastomeric member 148 may be removably attached to the elongate member 140 and in other embodiments the elastomeric member 148 may be permanently attached to the elongate member 140. In some embodiments, the elastomeric member 148 may be secured to the elongate member 140 with any desired means, for example, an adhesive, insert molded, press fit, interlocking, threaded connection, or any other method that will suitably secure the elastomeric member 148 to the elongate member 140. In other embodiments, the elastomeric member 148 may not be physically secured to the elongate member 140, but instead may be placed over the elongate member 140 in a friction fit or any other suitable manner.

Figure 8A:
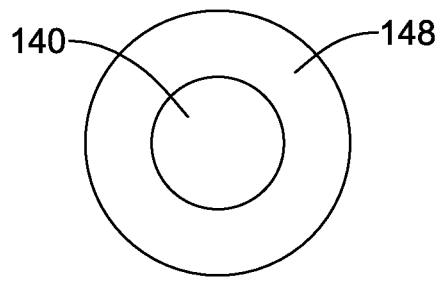
FIGS. 8A-8C are axial cross sections of alternate embodiments of the elongate member shown in FIG. 8
Figure 8B:
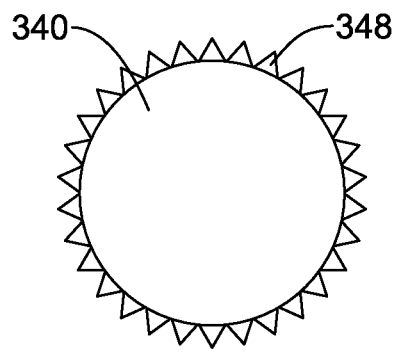
Figure 8C:
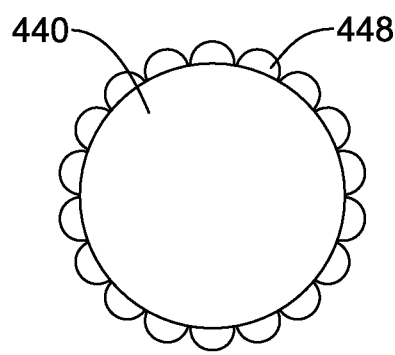

FIG. 8A shows a cross-section of the illustrative elongate member 140 shown in FIG. 8. The elastomeric member 148 is shown having an annular cross-section, but it is contemplated that the elastomeric member 148 may have any cross-section necessary to cooperate with the elongate member 140. The elastomeric member 148 is shown in FIG. 8A as having a continuous, smooth surface. It is contemplated that the elastomeric surface may comprise a plurality of elastomeric members 348, 448 as shown in FIGS. 8B and 8C. The elastomeric members 348, 448 may be of any shape or size desired. It is contemplated that the elastomeric member 148 may also comprise a unitary member with a textured surface, such as that created by the elastomeric members 348, 448 in FIGS. 8B and 8C.

FIGS. 9-13 illustrate alternative embodiments for a locking member 50, 150 and the elastomeric member 60, 160 which may be used with a fastener 15. One of skill in the art would understand that the features described in FIGS. 9-13 are not meant to be exclusive to each embodiment and are only illustrative of some possible combinations. The features of each embodiment may be interchangeable with the features of other embodiments.

In the illustrated embodiments, the locking member 50 may have a first end region 54 and a second end region 56 and a threaded region 52 disposed therebetween. Elastomeric member 60 is shown secured to the second end region 56 or within the second end region 56 of the locking member 50. In some embodiments, the elastomeric member 60 may be removably attached to the locking member 50 and in other embodiments the elastomeric member 60 may be permanently attached to the locking member 50. In some embodiments, the elastomeric member 60 may be secured to the locking member 50 with any desired means, for example, an adhesive, insert molded, press fit, interlocking, threaded connection, or any other method that will suitably secure the elastomeric member 60 to the locking member 50. In other embodiments, the elastomeric member 60 may not be physically secured to the locking member 50, but may be may be held between the elongate member 40 and the locking member 50 by the force of the locking member 50.

Figure 9:
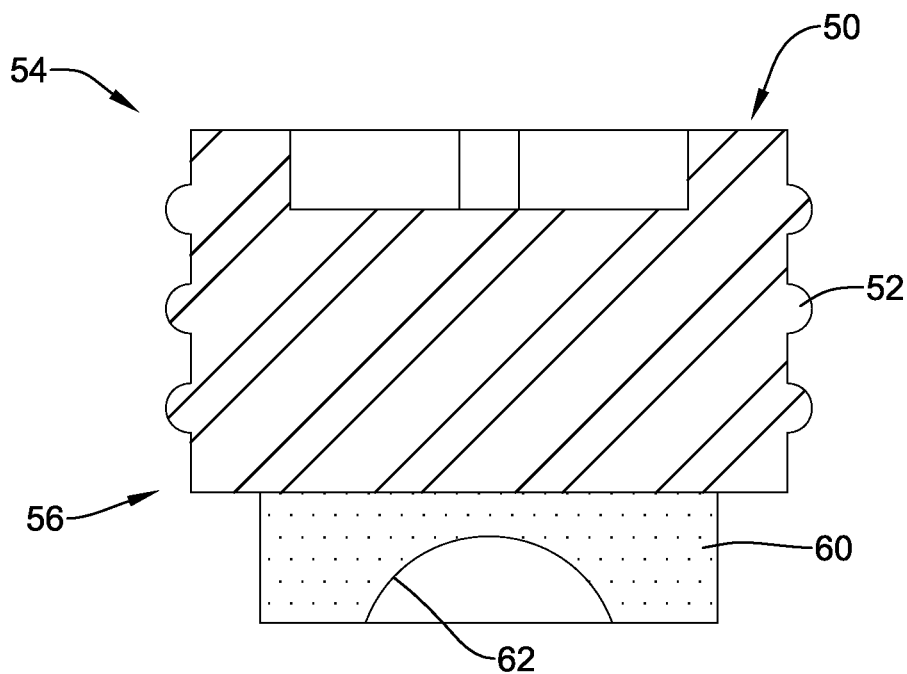
FIGS. 9-13 are alternate embodiments of the locking member and elastomeric member which may be used with a fastener of a spinal fixation assembly.

FIG. 9 shows an axial cross section of one embodiment of locking member 50. Locking member 50 may be a set screw having a region of external threading 52 between the first end region 54 and the second end region 56. Elastomeric member 60 may be secured directly to the surface of the second end region 56 of locking member 50. In this embodiment, the elastomeric member 60 may be secured such that it does not extend past the surface of the second end region 56 or into an interior region of the second end region 56. In some embodiments, the elastomeric member 60 may further comprise a concave recess 62 similar to the concave recess 72 shown in FIG. 3, which may sized and configured to receive a portion of the spherical collar 42. In other embodiments, the recess 62 may be of any desired shape to receive a collar 42 of any desired shape. It is also contemplated that the recess 62 may extend the entire depth of the elastomeric member 60 to form a concave channel configured to receive the elongate member 40 therethrough.

Figure 10:
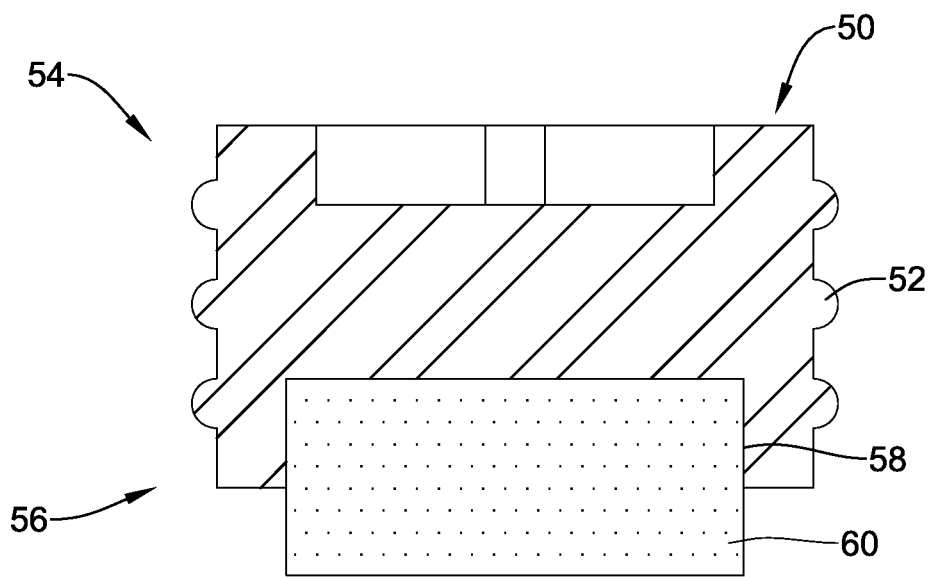

FIG. 10 shows an axial cross section of an alternative embodiment of locking member 50. Locking member 50 may be a set screw having a region of external threading 52 between the first end region 54 and the second end region 56. In this embodiment, locking member 50 may further include a bore 58 having a diameter smaller than the outer diameter of the locking member 50. Elastomeric member 60 may extend into the bore 58 of locking member 50. In some embodiments, the diameter of elastomeric member 60 may be substantially the same as the diameter of the bore 58. In other embodiments, the diameter of the elastomeric member 60 may be larger than the diameter of the bore 58 prior to be pressed or otherwise disposed into the bore 58.

Figure 11:
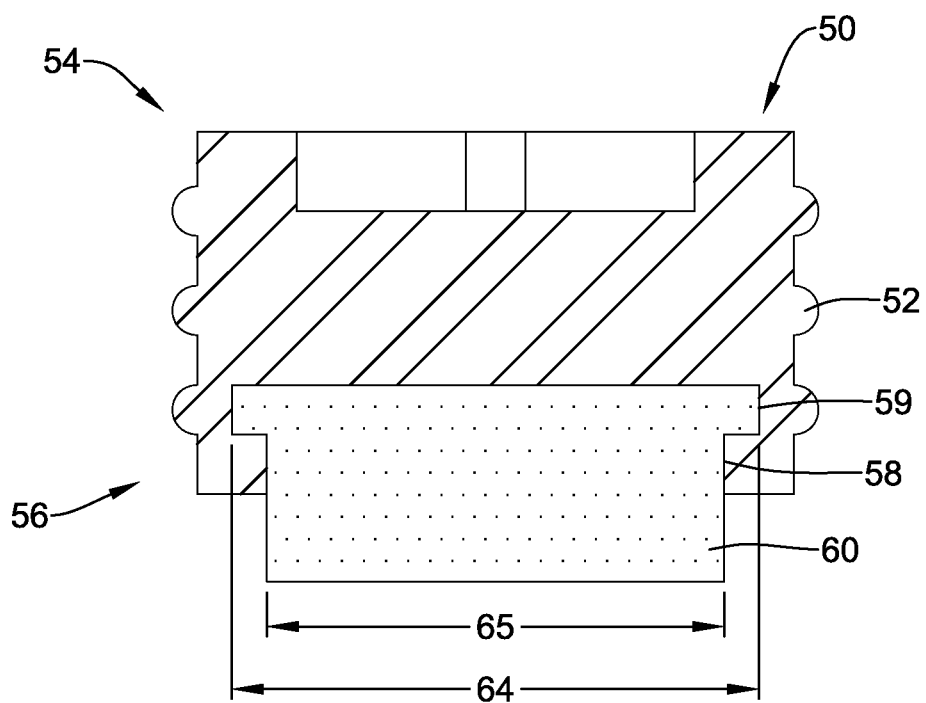

FIG. 11 shows an axial cross section of another embodiment of locking member 50. Locking member 50 may be a set screw having a region of external threading 52 between the first end region 54 and the second end region 56. In this embodiment, locking member 50 may further comprise a bore 58 having a diameter smaller than the outer diameter of the locking member 50. The bore 58 may further comprise an annular groove 59 at the end of the bore 58 towards the first end region 54 of the locking member 50. In other embodiments, the annular groove 59 may be at any longitudinal location along the height of the bore 58. The annular groove 59 may have a diameter larger than the diameter of the bore 58. Elastomeric member 60 may extend into the bore 58 and further into the annular groove 59. In some embodiments, the elastomeric member 60 may have a first diameter 64 substantially equal to the diameter of the bore 58 that extends from the portion of the elastomeric member 60 external to the locking member 50 to the annular groove 59 and a second diameter 65 substantially equal to the diameter of the annular groove 59. In other embodiments, the elastomeric member 60 may have a diameter substantially equal to the diameter of the annular groove 59 along its entire length, which may result in the elastomeric member 60 being compressed in the bore 58 and returning to a diameter substantially equal to the diameter of the annular groove 59 external to the locking member 50.

Figure 12:
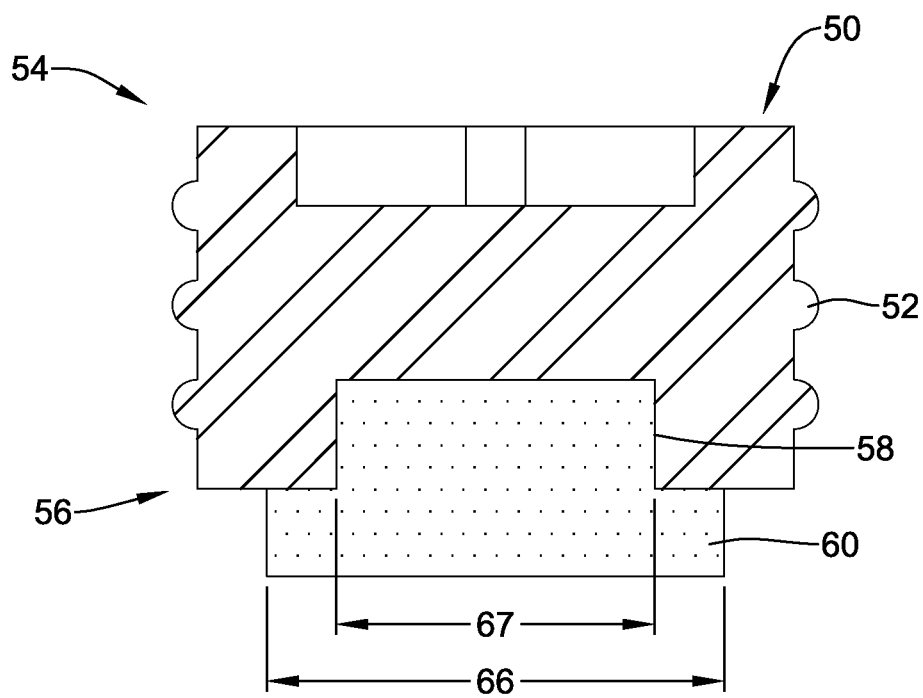

FIG. 12 shows an axial cross section of another embodiment of locking member 50. Locking member 50 may be a set screw having a region of external threading 52 between the first end region 54 and the second end region 56. In this embodiment, locking member 50 may further comprise a bore 58 having a diameter smaller than the outer diameter of the locking member 50. Elastomeric member 60 may extend into the bore 58 of locking member 50. Elastomeric member 60 may have a first diameter 67 internal to the locking member 50 which may be substantially the same diameter as the bore 58 and a second diameter external to the locking member 50 that may be larger than the diameter of the bore 58. Alternatively, the elastomeric member 60 may have a diameter larger than the diameter of the bore and may be compressed within the bore 58. This may result in the diameter 66 of the elastomeric member 60 external to the locking member 50 being larger than the diameter of the bore 58. In either embodiment, the diameter of the elastomeric member 60 external to the bore 58 may be smaller than the diameter of the locking member 50.

Figure 13:
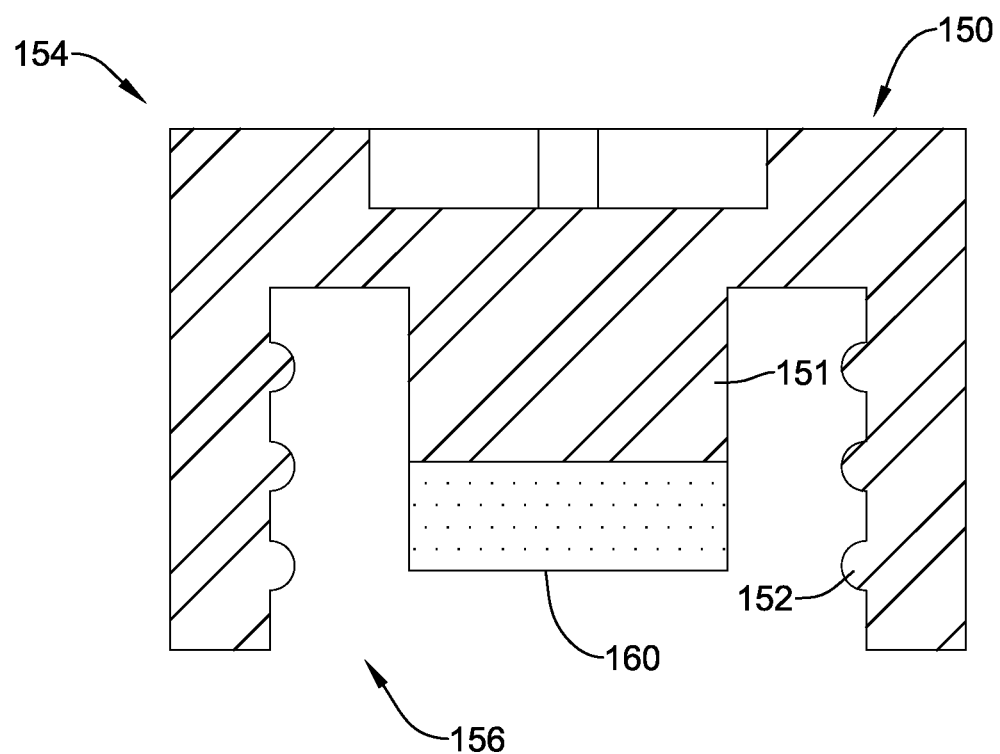

FIG. 13 shows an axial cross section of another alternative embodiment of a locking member 150. In some embodiments, the locking member 150 may be a cap having a region of internal threading 152 to complement external threading of the second end region 30 of a fastener 15. The locking member may have a first closed end region 154 and a second open end region 156. The locking member 150 may further comprise a protrusion 151 extending perpendicularly from an inner surface of the first closed end region 154 of the cap 150. Elastomeric member 160 may be secured to the protrusion 151 extending from the locking member 150. Elastomeric member 160 may be secured to the locking member protrusion 151 with an adhesive, insert molded, press fit, interlocking fit, threaded connection, or any other method that will suitably secure the elastomeric member 160 to the protrusion 151. In some embodiments, the diameter of elastomeric member 160 may be smaller than or substantially equal to the diameter of the protrusion 151 extending from locking member 150. Elastomeric member 160 may be directly secured to protrusion 151 of locking member 150. In this embodiment, the elastomeric member 160 may be secured such that it does not extend past the surface of the protrusion 151 or into an interior region of the protrusion 151. However, in other embodiments, the configuration of the member 160 with respect to the locking member 150 may be substantially similar to those discussed in FIGS. 6-9, or other desired configurations.

FIGS. 14-17 illustrate alternative embodiments for the second end region 30,130 and the elastomeric member 70,170 of a fastener 15. One of skill in the art would understand that the features described in FIGS. 11-14 are not meant to be exclusive to each embodiment and are only illustrative of some possible combinations. The features of each embodiment may be interchangeable with the features of other embodiments. In some embodiments, the elastomeric member 70 may be removably attached to the second region 30 and in other embodiments the elastomeric member 70 may be permanently attached to the second region 30. In some embodiments, the elastomeric member 70 may be secured to the second region 30 with any desired means, for example, an adhesive, insert molded, press fit, interlocking, threaded connection, or any other method that will suitably secure the elastomeric member 70 to the second region 30. In other embodiments, the elastomeric member 70 may not be physically secured to the second region 30, but instead may be held between the elongate member 40 and the second region 30 by the force of the elongate member 40 and a locking member 50.

Figure 14:
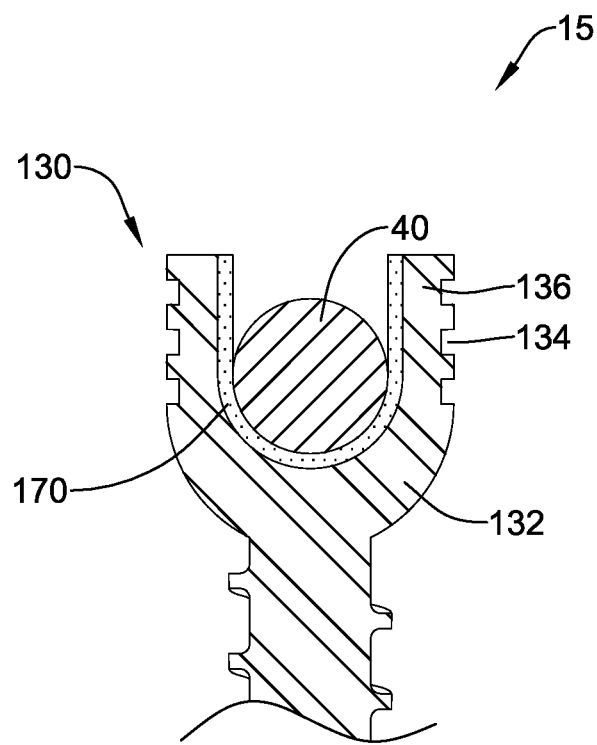
FIGS. 14-17 are alternate embodiments of the second end region of a threaded fastener and elastomeric member which may be used in a spinal fixation assembly.

FIG. 14 shows an axial cross section of an alternate embodiment of the second region 130 of the threaded fastener 15. Second region 130 may have a U-shape saddle 132 with a region of external threading 134. In some instances, this embodiment of a fastener 15 may be used with a cap locking member 150 as shown in FIG. 10. The cap locking member 150 used in combination with the externally threaded second end region 130 may result in the spinal fixation assembly having a reduced profile as the second region 130 may be smaller. When locking member 150 is threadably engaged with second region 130, the elastomeric member 160 and the elastomeric member 170 may contact and/or conform to the elongate member 40. In some embodiments, the elastomeric member 170 may be flush with or directly secured to the internal wall 136 of the saddle 132. In this embodiment, the elastomeric member 170 may be directly connected to the internal wall 136 of the saddle 132 such that the elastomeric member 170 does not break the plane of the internal wall 136. In this embodiment, the elastomeric member 170 may reduce the volume of the channel extending through the saddle 132 of the second region 130. In some embodiments, the elastomeric member 170 may extend to the top and/or toward the top of the saddle 132. In other embodiments, the elastomeric member 170 may extend up only a portion of the wall 136. In some embodiments, the elastomeric member 170 may be secured to the second end region 130 with any desired means, for example, an adhesive, insert molded, press fit, interlocking, threaded connection, or any other method that will suitably secure the elastomeric member 170 to the second end region 130.

Figure 15:
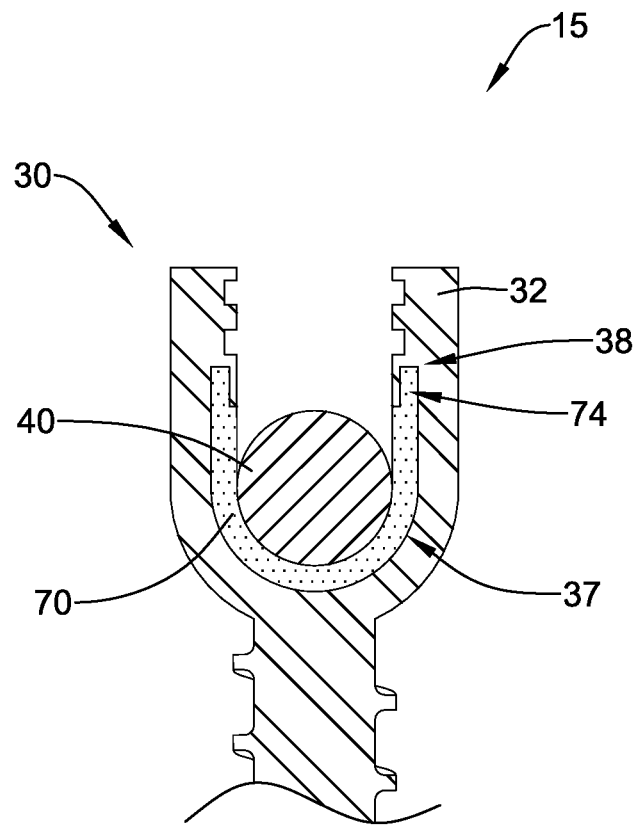

FIG. 15 shows an axial cross section of another embodiment of the second region 30 of the fastener 15. In this embodiment, the saddle 32 may further comprise an internal recess 37. The elastomeric member 70 may be positioned in the internal recess 37. In some embodiments, the elastomeric member 70 may have a thickness such that the elastomeric member 70 does extend into an interior region of the saddle 32 past an inner surface of the saddle 32 of the second end region 30. In other embodiments, the elastomeric member 70 may have a thickness such that the elastomeric member 70 extends past an inner surface of the saddle 32 of the second region 30 and extends into an interior region of the channel of the U-shape saddle 32. In some embodiments, the recess 37 may further comprise a groove 38. The groove 38 may be positioned toward the top region of the U-shape saddle 32. A tabbed portion 74 of the elastomeric member 70 may extend into the recess 38 such that the tabbed portion 74 of the elastomeric member 70 is disposed behind a portion of the inner wall 36 of the saddle 32, e.g. within the recess 38. The recess 38 and tabbed portion 74 may help maintain the position of the elastomeric member 70 within the second region 30 of the fastener 15.

Figure 16:
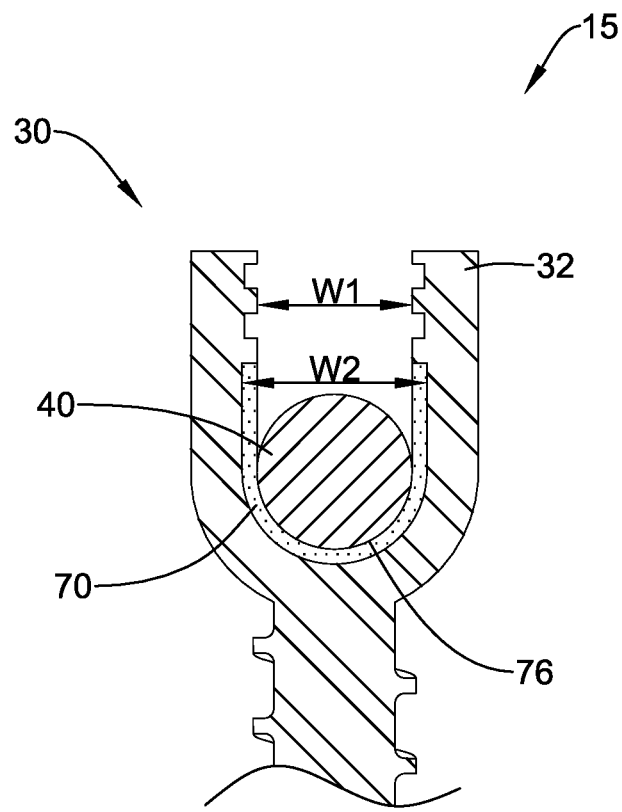

FIG. 16 shows an axial cross section of yet another embodiment of the second region 30 of the threaded fastener 15. As shown in this embodiment, in some instances, the second region 30 may have a first width W1 at the threaded region 34 and a second, larger width W2 in the portion of the channel including the elastomeric member 70. The elastomeric member 70 may be disposed within the channel 32 such a distance between the inner surfaces of the elastomeric insert 70 is substantially equal to the first width W1, creating a continuous surface along the interior region of the second region 30. Elastomeric member 70 may further comprise a recess 76 for receiving the elongate member 40. The recess 76 may form a concave channel that may contact and/or conform to the elongate member 40. In some embodiments, recess 76 may conform to the elongate member 40. The recess 76 may allow more surface area of the elongate member 40 to contact the elastomeric member 70, which may allow for a more uniform clamping force to be applied to the elongate member 40. This may reduce slippage of the elongate member 40 while allowing a certain degree of dynamic angular movement. It is contemplated that in some embodiments, the recess 76 may extend the entire depth of the second region 30 from a first side surface to a second side surface or across only a portion of the depth of second region 30. The recess 76 may be slightly smaller than the elongate member 40 such that the elastomeric member 70 is slightly compressed to receive to the elongate member 40 within the recess 76 of the member 70. In other embodiments, the recess 76 may be substantially the same size as the elongate member 40 or slightly larger than the elongate member 40.

Figure 17:
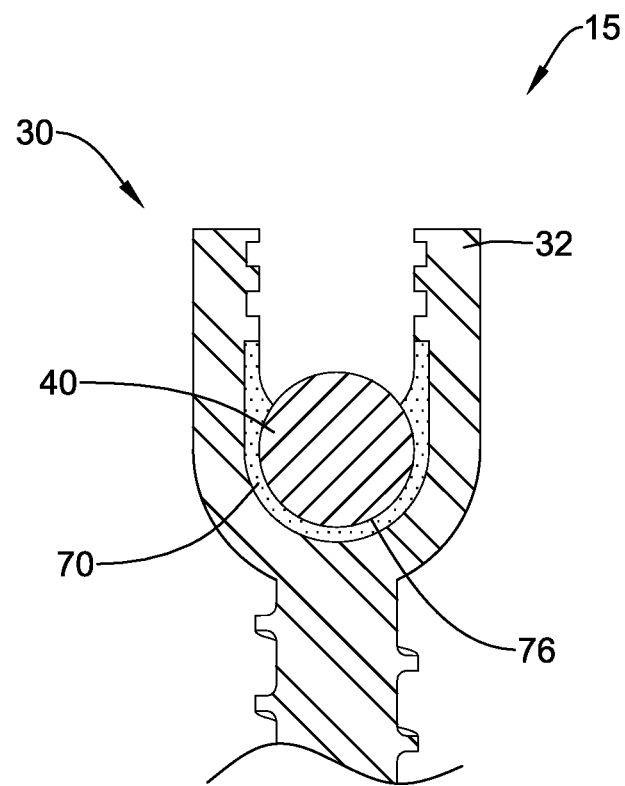

FIG. 17 shows an axial cross section of another alternative embodiment of the second end region 30 of the threaded fastener 15. As shown in this embodiment, in some instances, the elastomeric member 70 may be disposed within an interior wall of the saddle 32 of the second region 30 such that the elastomeric member 70 and the interior surface of the second region create a continuous surface. Elastomeric member 70 may further comprise a recess 76 for receiving the elongate member 40. The recess 76 may form a concave channel that may contact and/or conform to the elongate member 40. In some embodiments, the recess 76 may have a depth larger than half the perimeter, e.g. circumference, of the elongate member 40 such that the elastomeric member 70 begins to wrap around an upper side of the elongate member 40. To some degree, the recess 76, which may extend around and/or be in contact with greater than 50% of the perimeter, e.g. circumference, of the elongate member 40, may maintain the elongate member 40 in a given position without the use of the locking member 50. In some embodiments, the elongate member 40 may snap into the recess 76 of the elastomeric member 70. Alternatively, the elongate member 40 may be slid into the recess 76 of the elastomeric member 70. In some embodiments, recess 76 may conform to the shape elongate member 40. Further, the recess 76 in the elastomeric member 70 may reduce the amount of slippage of the elongate member 40 while allowing a certain degree of dynamic axial movement between the elongate member 40 and the second region 30 of the fastener 15. It is contemplated that in some embodiments, the recess 76 may extend the entire depth of the second end region 30 from a first side surface to a second side surface or across only a portion of the depth of second end region 30 to form a concave channel that may contact and/or conform to the elongate member 40.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

I claim:

1. A spinal fixation assembly comprising:
   a fastener having a first region configured for attachment to a vertebra of a patient and a second region including a channel configured to receive an elongate member, the second region including a first polymeric member on a wall of the channel and wherein the first polymeric member configured to engage the elongate member and elastically deform against the elongate member; and
   a locking member for securing the elongate member within the channel of the second region, wherein the locking member includes a second polymeric member disposed on the locking member, the second polymeric member configured to engage the elongate member and elastically deform against the elongate member.

2. The spinal fixation assembly of claim 1, wherein the locking member is a set screw having a first end, a second end, and a bore extending from a second end towards a first end for receiving the second polymeric member.

3. The spinal fixation assembly of claim 2, wherein a portion of the second polymeric member extends past a surface of the second end of the set screw.

4. The spinal fixation assembly of claim 3, wherein a portion of the second polymeric member external to the set screw has a diameter larger than a diameter of the bore.

5. The spinal fixation assembly of claim 2, wherein the bore further comprises an annular groove towards the first end of the set screw.

6. The spinal fixation assembly of claim 5, wherein the second polymeric member extends into the bore and the annular groove.

7. The spinal fixation assembly of claim 1, wherein the second region is configured to threadably receive the locking member.

8. The spinal fixation assembly of claim 7, wherein the second region of the fastener further comprises a slot for receiving the first polymeric member.

9. The spinal fixation assembly of claim 1, wherein the locking member is a set screw having a first end, a second end, and a diameter that is larger than a diameter of the second polymeric member.

10. The spinal fixation assembly of claim 9, wherein the second polymeric member is secured directly to a surface of the second end of the set screw.

11. The spinal fixation assembly of claim 1, wherein when the elongate member is secured to the fastener, the polymeric members provide for a degree dynamic angular displacement of the elongate member within the channel of the second region of the fastener.

12. The spinal fixation assembly of claim 1, wherein the second region is 'U'-shaped.

13. The spinal fixation assembly of claim 1, wherein the first and second polymeric members comprise a polyurethane.

14. The spinal fixation assembly of claim 1, wherein the locking member is a cap having internal threads.

15. The spinal fixation assembly of claim 1, wherein the first polymeric member further comprises a recess for receiving the elongate member.

16. A spinal fixation assembly comprising:
   a fastener having a first region and a second region, the second region defining a channel;
   an elongate member extending through the channel of the second region of the fastener;
   a first polymeric member disposed on a wall of the channel for engagement with the elongate member in the channel, wherein the first polymeric member is positioned between the elongate member and the second region of the fastener; and wherein the first polymeric member is in contact with the elongate member and allows for dynamic angular displacement of the elongate member relative to the second region of the fastener; and
   a locking member for securing the elongate member within the channel of the second region of the fastener, wherein the locking member includes a second polymeric member disposed on the locking member, the second polymeric member contacting the elongate member to allow dynamic angular displacement of the elongate member relative to the locking member.

17. The spinal fixation assembly of claim 16, wherein the elongate member comprises one or more spherical collars.

18. The spinal fixation assembly of claim 17, wherein the elongate member and the one or more spherical collars form a unitary member.

19. The spinal fixation assembly of claim 17, wherein the first polymeric member comprises a concave recess for receiving the spherical collar.

20. The spinal fixation assembly of claim 16, wherein the second polymeric member is positioned between the elongate member and the locking member.

21. The spinal fixation assembly of claim 20, wherein the first and second polymeric members are in contact with the elongate member and allow for dynamic angular displacement of the elongate member relative to the second region of the fastener.

22. The spinal fixation assembly of claim 16, wherein the first polymeric member is disposed on a surface of the channel of the second region of the fastener.

23. The spinal fixation assembly of claim 16, wherein the elongate member is spaced from the locking member by the second polymeric member.

24. The spinal fixation assembly of claim 16, wherein the elongate member comprises one or more spherical collars and the second polymeric member comprises a concave recess for receiving the spherical collar.

25. The spinal fixation assembly of claim 16, wherein the second region is 'U'-shaped.

26. The spinal fixation assembly of claim 16, wherein the second region is configured to threadably receive the locking member.

27. The spinal fixation assembly of claim 16, wherein the elongate member is spaced away from the second region of the fastener by the first polymeric member.

28. A method for coupling a spinal fixation assembly to a patient's spine, the method comprising the steps of:
 providing a fastener, the fastener comprising:
  a first region and a second region;
  the second region of the fastener defining a channel;
  a first polymeric member disposed on a wall of the channel;
 securing the fastener to the patient's spine;
 placing an elongate member within the channel of the second region such that the elongate member is in contact with the first polymeric member;
 providing a locking member, the locking member including a second polymeric member disposed on the locking member, the second polymeric member configured to engage the elongate member; and
 engaging the locking member with the second region of the fastener to secure the elongate member within the channel.

29. The method of claim 28, wherein the second polymeric member deforms around a portion of the elongate member.

30. The method of claim 28, wherein an elasticity of the first and second polymeric members allows for dynamic angular displacement of the elongate member within the channel of the second region of the fastener.

31. The method of claim 28, wherein the first polymeric member deforms around a portion of the elongate member.

32. The method of claim 28, wherein an elasticity of the first polymeric member allows for dynamic angular displacement of the elongate member within the channel of the second region of the fastener.

* * * * *